(12) United States Patent
Gozzini et al.

(10) Patent No.: US 6,719,958 B1
(45) Date of Patent: Apr. 13, 2004

(54) POLYCHELANTS, THEIR COMPLEXES WITH METAL IONS, THEIR PREPARATION AND THEIR USES

(75) Inventors: Luigia Gozzini, Milan (IT); Federico Maisano, Milan (IT); Marcella Murru, Milan (IT)

(73) Assignee: Dibra S.p.A., Milan (IT)

( * ) Notice: Subject to any disclaimer, the term of this patent is extended or adjusted under 35 U.S.C. 154(b) by 0 days.

(21) Appl. No.: 09/659,593

(22) Filed: Sep. 11, 2000

Related U.S. Application Data

(63) Continuation-in-part of application No. 09/117,358, filed as application No. PCT/EP97/01048 on Mar. 3, 1997.

(30) Foreign Application Priority Data

Mar. 8, 1996 (IT) .......................... MI96A0458

(51) Int. Cl.$^7$ .......................... A61K 31/33; A61K 49/12; C07D 257/00

(52) U.S. Cl. .................... 424/9.363; 514/183; 514/184; 534/15; 534/16; 540/465; 540/474

(58) Field of Search ..................... 534/15, 16; 540/465, 540/474; 514/183, 184; 424/9.363

(56) References Cited

U.S. PATENT DOCUMENTS 5,650,133 A  7/1997  Carvalho et al. .......... 424/1.65

FOREIGN PATENT DOCUMENTS

| EP | 0 661 279 A | 7/1995 |
|---|---|---|
| FR | 2 596 992 A | 10/1987 |
| WO | WO 95 27705 A | 10/1995 |

*Primary Examiner*—Richard L. Raymond
(74) *Attorney, Agent, or Firm*—Nixon & Vanderhye P.C.

(57) ABSTRACT

A new class of polychelants, their chelates with metal ions and their physiologically acceptable salts, useful, either as they are or in association or formulation with other components, for diagnostic imaging as general or specific contrast agents for specific tissues, organs or body compartments.

16 Claims, No Drawings

POLYCHELANTS, THEIR COMPLEXES WITH METAL IONS, THEIR PREPARATION AND THEIR USES

This application is a continuation-in-part of application Ser. No. 09/117,358, filed Jul. 28, 1998, now abandoned, the entire content of which is hereby incorporated by reference in this application, which is a 371 of PCT/EP97/01048, filed Mar. 3,1997.

The present invention concerns a new class of polychelants, their chelates with metal ions and their physiologically acceptable salts, which can be used, either as they are or in association or formulation with other components, for diagnostic imaging as general or specific contrast agents for specific tissues, organs or body compartments.

The new class of contrast agents is constituted by molecules or macromolecules obtained by covalently linking chelants or chelates of metal ions to a "carrier" composed of an organic "backbone" which carries at least two primary amino groups, to which said chelants/chelates are attached through alkylene bridges. This class is characterized by the fact that at least one or, preferably, more primary amino groups of the "carrier" have been bifunctionalised, (through reductive dialkylation) with alkylene residues carrying said chelants or metal chelates or their salts, while the other primary amino groups can be present either as such (i.e., non-functionalized salified or not), or monofunctionalized with said chelant/chelate residues, the total number of chelants/chelates moieties attached to said amino groups being at least three. This class of contrast agents usually contains a high number of chelant/chelate residues per molecule, which are attached to the primary amino groups present in the carrier. In fact, depending on the structure of this carrier, the reactivity of the amino groups and the reaction conditions, up to two chelant/chelate residues can be attached to each primary amino group.

This invention concerns also a peculiar process for the preparation of these molecules, as well as their uses.

Complexes formed of chelating agents and suitable metal ions are in use both in nuclear medicine and in magnetic resonance imaging (MRI). In nuclear medicine, radioactive metal chelates are used as both diagnostics (scintigraphy, PET or positron emission tomography) and therapeutics. In nuclear medicine, macromolecules with high biospecificity such as, for example, antibodies and more recently, polypeptides are widely used. In this latter case they are analogues (both agonists and antagonists) of biologically active polypeptides. An example of this approach is Octreoscan, a derivative of somatostatin carrying a complex of $^{111}In^{(3+)}$, which was developed to visualize and localize tumors of neuroendocrin origin. A problem presented by these derivatives concerns the intrinsic biological activity of the carrier (also called address) macromolecules, the doses of which must be such as to provide improved visualization of the organ under investigation, without inducing appreciable pharmacological actions. The possibility of increasing the number of diagnostically efficacious sites for carrier molecule would permit a reduction of the dose required to obtain the same diagnostic effect and therefore also a reduction of the possibility of undesired effects connected to the pharmacological activity of the molecule. This problem becomes more important when it is necessary not to modify a number of the amino groups, particularly those required for receptor recognition or biological activity. For example, it is known that the s-amino group of lysine in position B29 of insulin can be modified without compromising the biological activity, while none of the α-amino groups can be modified without altering the activity. The present invention, which enables the degree of substitution of the amino groups to be maximized, permits one to get around this problem and thus is highly advantageous for diagnostic techniques characterized by low sensitivity, such as, for example, MRI.

In the preparation of biospecific contrast agents for MRI, the most common approach has been first to react macromolecules, such as proteins and polylysine, with chelating agents having functional groups capable of conjugating the ε-amino group of lysine, preferably through formation of amide or analogous bonds, and then to complex the resulting compounds with gadolinium (for example, Ogan et al., Invest. Radiol., 1987, 22, 665–671). By this approach however it is not possible to link more than one chelant unit per amino group of the carrier. Indeed, the total number of chelant groups per protein is normally extremely low if compared with the total number of amino groups theoretically functionalizable on the molecule. For example, Lewis et al. (Bioconj. Chem., 1994, 5, 565–576) report the conjugation of the chelating agent DOTA (1,4,7,10-tetraazacyclododecan-N,N',N'',N'''-tetraacetic acid) to cytochrome c through activation with N-hydroxysulphosuccinimide. Increasing the molar ratio between the active ester of DOTA and cytochrome c from 10:1 to 100:1 results in increasing from 2.64 to 8.79 the average number of chelating groups attached to the protein, out of a total of 19 available primary amino groups.

In addition, the subsequent formation of the complex with gadolinium does not ensure that the same happens quantitatively. The overall result is that not all the amino groups are functionalized with chelating groups and that not all the chelating groups introduced become saturated with gadolinium. Neither does the state of the art teach to link the free amino groups of the macromolecules of interest directly with performed chelates, or their salts, in such a way as to obtain the maximum chelation possible. In this respect see the following documents: U.S. Pat. No. 4,855,353, EP-A-481526, EP-A-243929, EP-A-255471, WO 9514491, GB 2169598 B, EP-A-038546, WO 9014881, and US 5,650,133. In particular, the last one seeks to obtain, and actually discloses, dichelants prepared by attaching two macrocyclic ligands to the two different extremities of a linker moiety. The preparation is carried out in a completely traditional manner, i.e., reacting an activated carboxy group with an amino group (either primary or secondary), thus giving final products that are amido derivatives. No possibility of preparing two macrocyclic dichelants moieties linked to the same amino group is suggested (the traditional synthetic pathway adopted cannot in any case give such result, as already explained above). The preferred compounds, disclosed in Example 12, comprise linkers that are terminal diamino derivatives, either primary or secondary, said amino groups being joined to the two macrocyclic chelant moieties through amido bonds, every amino group carrying just one chelating moiety.

As a consequence, diagnostically optimal doses of said contrast media contain high quantities of macromolecular carrier, with the result that undesired biological effects may arise. It would be highly desirable to be able to transport efficacious doses of metal chelate with substantially lower quantities of macromolecular carrier. So the technical need to be solved is the preparation of compounds that carry the maximum possible number of metal complexes per molecule, thus giving a positive answer to the above-mentioned problems.

The present invention solves this problem by allowing the linking of up to two units of chelants, or, even better, directly of their metal complexes, to each individual primary amino group present on the structure. This structure can for example be a macromolecule such as a protein, a polymer or a peptide, an amino acid or even a simple diamine or a polyamine. This aspect of the invention is particularly useful for those cases in which one or more primary amino groups of the address molecule must be maintained as such (for example after selective, easily removable protection) to preserve biological activity or tissue organ specificity (see the case cited above for insulin). Also in these cases the dialkylation of the other primary amino groups of the carrier with suitable chelant/chelate groups, according to the teaching of the present invention, yields a number of diagnostically or therapeutically active sites per molecule that is greater than that which is obtainable according to the current state of the art.

The same can be said for those polyamino carriers in which not all the primary amino groups usually undergo modification, because, for example, they are not equally sterically accessible. Also in this case, the possibility of attaching two chelant/chelate residues at least on a single primary amino group consents to get final products that are more substituted an consequently more efficacious than those obtained by the current known methods. An example from the state of the art is given by the above cited patent application WO 9514491 which reports the preparation of diagnostic agents based on the 1:1 ion-pair Gd-DTPA-Lysine and dermatan sulphate (in the example of page 77), able to selectively visualize endothelial structures. Also, in this case the ratio between chelant/chelate residues and the amino groups on the lysine are not greater than unity (there is in fact only one chelate group against two lysine primary amino groups). On the contrary, according to the specific process of the present invention, it is possible to obtain lysine derivatives with at least two chelant/chelate residues on one of the two amino groups, or even, two chelant/chelate residues for each one of the primary amino groups (for a total of four chelant/chelate groups against two amino groups, see examples 3 to 6 below), with the resulting advantages that:

(a) the quantity of dermatan sulphate necessary to obtain the same diagnostic effect is at least halved, as are, in consequence, also its anticoagulant effects, (b) the resulting ion-pair is further stabilized by the high positive charge of the lysine derivative, since, in this case, the original amino groups are not mono-acylated (as in WO 9514491), but di-alkylated.

In addition, the present invention gives access to multiple Gd chelates that have a relaxivity $r_1$ which is increased over the value of the single chelates, also when calculated on the basis of the number of Gd ions. When a chelate is grafted to a macromolecule an increase in $r_1$ is expected; compare, for example, the myoglobin conjugate of Example 12, having $r_1$=19 mM$^{-1}$s$^{-1}$ on a per gadolinium basis, with the $r_1$ value for Gd-DOTA (3.4 mM$^{-1}$s$^{-1}$ according to the literature: e.g., Lauffer R. B. (1990) *Magn. Reson. Quart.* 2, 65–84). However, we show that it is also possible to prepare multiple Gd chelates of enhanced relaxivity and relatively low-molecular mass (see Example 6 for a lysine derivative, whose relaxivity has more than doubled from 3.4 of Gd-DOTA to 8.35 mM$^{-1}$s$^{-1}$, on a per gadolinium basis). When this effect is combined with the increased number of chelated Gd ions a very high molecular relaxivity is obtained, with consequent substantial reduction of the efficacious dose.

Therefore an object of the present invention is a new class of polychelants/polychelates, and their biologically compatible salts, which are obtained from an organic polyaminic backbone carrying "m" primary amino groups, where "m" is a number from 2 to 1000, where the amino groups are alkylated, via reductive alkylation, with "n" chelant/chelate residues, being "n" a number from 3 to 2m, the cheland/chelate residues are covalently linked to the amino groups by means of an aliphatic chain, which is interrupted or not by heteroatoms selected from 0, N, S, or by groups selected from carbonyl, thiocarbonyl, amide, ester, thiourea, and thioamide groups, and where a number "p" of the amino groups, where "p" is a number from 0 to m-2, is non-functionalized, the compounds characterized by at least one of the primary amino groups is dialkylated with two of the chelant/chelate residues and, when the number "n" of the chelant/chelate residues on the molecule is 3, then one of the primary amino groups is monoalkyltaed with one of the chelant/chelate residues.

As a result, the number "n" of chelant/chelate residues on the molecule is always greater than the number of alkylated primary amino groups (which corresponds to m-p). In 5 mathematical terms the situation can be expressed by the following disequation:

$$n > m-p,$$

where m, n and p have the meanings described previously. In other words, defining ρ as the ratio between the number of chelant/chelate residues inserted on the "carrier" and the total number of alkylated primary amino groups (mono and dialkylated), the ratio must always be to greater than unity, that is:

$$\rho = \frac{n}{m-p} > 1$$

Furthermore, since the maximum possible number of chelant/chelate groups per primary amino group is 2, ρ too cannot be greater than this value. We can say therefore that for the compounds of the invention:

$$1 < \rho < 2$$

This parameter ρ, represents in a short way the main characteristic of the invention and differentiates the same from the state of the art, where ρ is always equal to unity, because the 20 maximum number of chelant units that can be attached to the primary amino groups of the organic backbone, by using synthetic methods usually employed in the art, is equal to the number of said amino groups, i.e., at best only a 1:1 ratio of functionalization is possible. The positive solution given by the present invention to the problem discussed above has been made possible thanks to the unexpected success achieved by developing a different synthetic pathway that, against the general teaching of the art, permits the bifunctionalization (dialkylation) with good yields of primary, even hindered, amino groups, by reacting them with suitable aldehydes, linked to the chelant/chelate moieties, under strictly controlled reductive conditions. In such way, the compounds of the invention are prepared by a specific synthetic process, which is disclosed below and which is also part of the invention.

Also a part of the present invention are the complexes of the various chelants with the bivalent or trivalent ions of elements having atomic numbers between 20 and 31, or 39, 42, 43, 44, 49, or between 57 and 83 and their physiologically compatible salts. Particularly preferred are $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $La^{(3+)}$, $Yb^{(3+)}$ or $Mn^{(2+)}$ or the ions of the following radioisotopes $^{51}Cr$, $^{67}Ga$ $^{68}Ga$ $^{111}In$, $^{99m}TC$, $^{140}La$ $^{175}yb$, $^{153}Smt$ $^{166}Ho$, $^{90}y$ $^{149}pm$ $^{177}LU$ $^{47}Sc$ $^{142}pr$, $^{159}Gd$, $^{22}Bi$.

One of the objects of the present invention are therefore polychelants or polychelates and their physiologically acceptable salts of formula (I):

(I), in which

L is a polyamine organic moiety;

F is a —$CH_2$—T—K group, representing a chelant/chelate residue, where

T is a $C_2$–$C_5$ aliphatic chain, interrupted or not by one or more heteroatoms selected from O, N, S or by functional groups selected from carbonyl, thiocarbonyl, amide, ester, thiourea or thioamide groups, said chain being linked covalently to a N atom of a residue K, K is the residue of a linear or cyclic polyaminopolycarboxylic or polyaminopolyphosphonic or polyaminopolyphosphoric or polyaminopoly-phosphinic chelant, or one of its metal chelates, or one of its salts, and where the total number of the F groups ranges from 3 to 2 m;

| | |
|---|---|
| p | is a number from 0 to m − 2, |
| z | is a number from 0 to m − 1, and |
| x | is a number from 1 to m, | where m is a number from 2 to 1000, m being the total number of the primary amino groups originally present on L, and where p+x+z=m, with the proviso that, when x=1, then z≠0, and in which the chelated metal ions are bi- or trivalent paramagnetic ions or radioisotopes.

For the purpose of the invention, any physiologically acceptable polyamine can be used as L, from the simplest diamines up to macromolecules and biomolecules carrying from 2 to 1000 primary amino groups. The choice will be made according to the diagnostic or therapeutic need. Nevertheless, a short exemplifying list, which is absolutely non-limitative for the invention, is disclosed below, among the preferred compounds.

A first class of preferred compounds comprises those in which:

Lis selected from the group constituted by: spermidine, spermine, norspermidine, 4,9-dioxadodecandiamine, 3,6-dioxaoctandiamine, alkylenediamines, diethylenetriamine, triethylenetetramine, tris-(2-aminoethyl)amine, jeffamine, lysine and derivatives, ornithine, insulin, chymotrypsinogen A, myoglobin, albumin, cytochrome c, branched and linear polylysine, branched and linear polyornithine, di- and polyamino sugars, polypeptides, hormones, growth factors, antibodies;

T is a $C_2$–$C_5$ aliphatic chain, containing an ester, amide or carbonylamino group, said chain being linked covalently to a nitrogen atom of a K residue, K is the residue of a polyaminopolycarboxylic acid selected from the group comprising: EDTA, DTPA, BOPTA, EOB-DTPA, DOTA, their derivatives, their metal chelates or salts, where the metal ion chelates are selected from the bi- or trivalent ions of elements having atomic numbers between 20 and 31, or 39, 42, 43, 44, 49, or between 57 and 83 or the ions of the following radioisotopes $^{51}Cr$ $^{67}Ga$, $^{68}Ga$, $^{111}In$ $^{99m}Tc$, $^{40}La$, $^{175}Yb$, $^{153}Sm$, $^{166}Ho$, $^{90}Y$ $^{149}Pm$ $^{177}Lu$, $^{47}Sc$ $^{142}pr$, $^{159}Gd$ or $^{212}Bi$.

A second class of preferred compounds is the one in which F is a residue of formula (II) or (III)

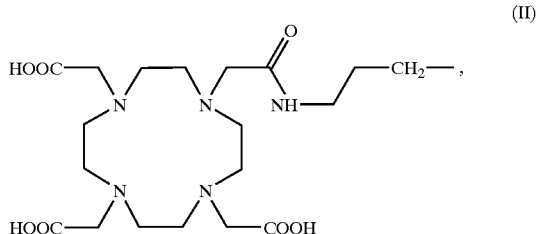

(II)

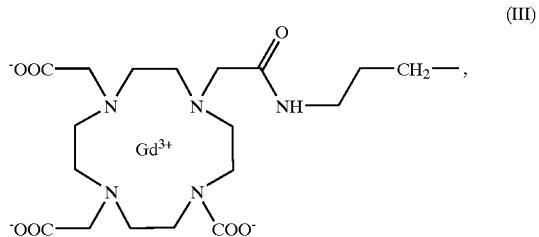

(III)

or of formula (IV) or (V)

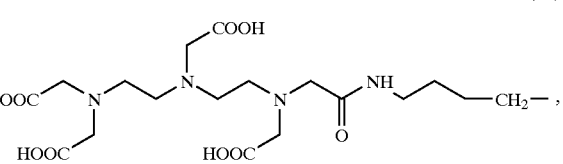

(IV)

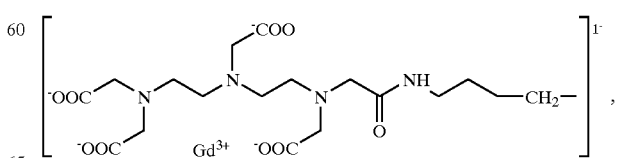

(V)

or one of their salts.

A third class of preferred compounds includes the

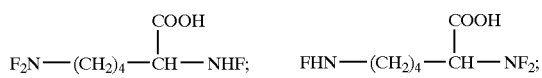

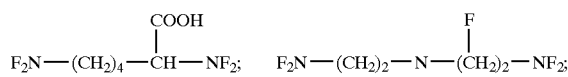

where F is a chelant residue of formula (II),

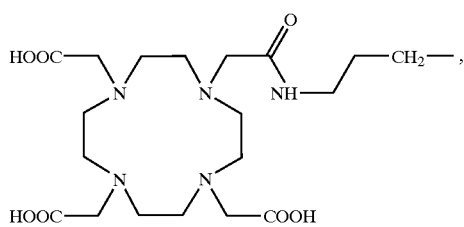

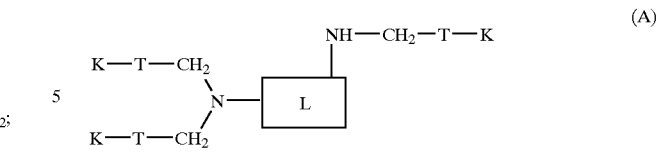

where L, K, T, are defined as above. The product illustrated in formula (A) was obtained starting from an organic diamine L containing 2 primary amino groups (m=2), one of which was dialkylated with two K—T—CH$_2$—residues while the other one was monoalkylated with one K—T—CH$_2$ residue. The resulting compound therefore contains two chelant/chelate moieties on one nitrogen (n=2) and one chelant/chelate residue on the other nitrogen (n=1). In total n=3. Since m−p is equal to 2, therefore n>m−p. Consequently, p=1.5, i.e., >1. A product of this type is disclosed in Example 4.

Analogously, in formula (B) below the structure is schematized of a polychelant/polychelate derivative, an object of the present invention, obtained starting from a polyaminic organic backbone L containing 19 primary amino groups (m=19).

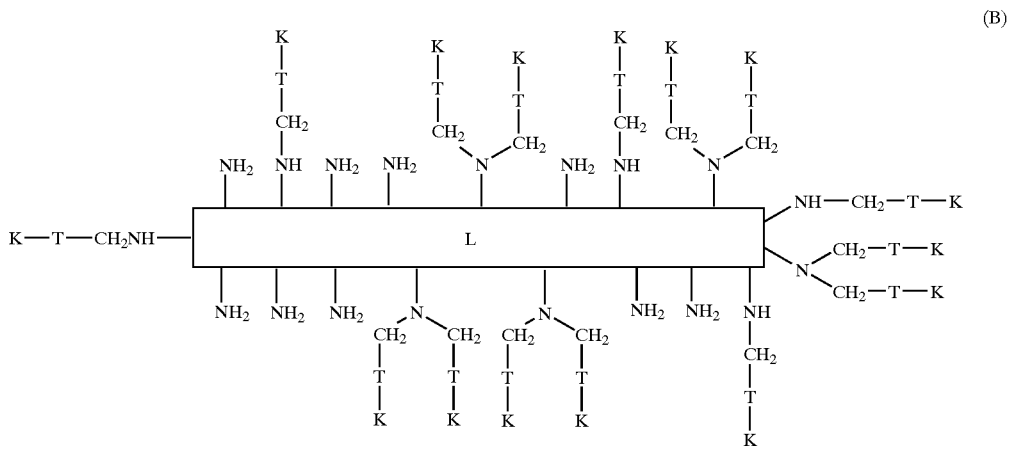

or a chelate of formula (III),

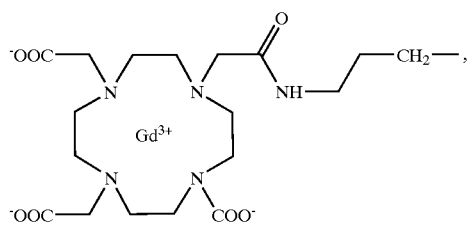

or a salt thereof. Other preferred compounds are those in which F is a residue of formula (II) or (III) and L is selected from the group constituted by insulin, myoglobin, albumin, cytochrome c, chymotrypsinogen A, polylysine.

To clarify the structure of the compounds of the invention, as an example, in formula (A) below the structure of a polychelant/polychelate derivative, object of the present invention is schematized The backbone L was alkylated according to the process of the invention. 15 K—T—CH$_2$-residues were attached, in total, to L. The final compound possesses 9 free unreacted primary amino groups (p=9) and a total of 15 alkylene groups (n=15). Since m−p is equal to 10, therefore n>m−p and p=1.5, that is >1. A product of this type is described in Example 11.

In principle, the compounds of the present invention can, for example, be obtained by any of the synthetic processes known to those skilled in the alkylation of primary amines such as alkylation with alkyl halides. Nevertheless, it is well known that dialkylation of primary, sometime hindered, amino groups, as in the case of biomolecules or polyamines, can be quite difficult, if not impossible, when the alkylating agent is a large group, like for example a macrocyclic chelating moiety. At best, it is possible to partially obtain only monoalkylated products, even with a small percentage of dialkylation, by employing drastic reaction conditions, long times and great excess of alkylating agent. Obviously the final compound is obtained with low yields and rich in such a number of impurities that the final purification results very difficult and too expensive. We have now surprisingly found that, in contrast to the prevailing teaching of the art, reductive alkylation can be a useful method and is particularly efficient for the preparation of the tertiary hindered amines that are the object of the present invention, as disclosed in more detail in Example 3 below. Indeed, a vast quantity of literature references exists (G. E. Meares & R. E. Feeney, Anal. Biochem. 224, 1–16, 1995) in which the use of reductive alkylation is described for the conjugation of different aldehydes with proteins in the presence of suitable reducing agents. However, with the sole exception of formaldehyde, the formation of tertiary amines is not observed. This is attributed to the reciprocal steric hindrance between the amine and the aldehyde. Recently, it has been reported that with a less sterically hindered amine such as glycine the formation of the tertiary amine can occur, but only in a very low percentage, as a by-product of the reaction (J.-P. Sani et al., Tetrahedron Lett. 35, 1181–1184, 1994). Even in another very recent article, where the reductive alkylation of proteins by aldehyde derivatives of chelating agents was described, there is no disclosure of double alkylation in spite of the careful optimization of various experimental parameters (V. V. Somayaji et al., Appl. Radiat. Isot. 47(1), 71–77, 1996). On the contrary, we have surprisingly found that under particular experimental conditions the steric hindrance of the two reagents is no longer a limiting factor. Namely tertiary amines can be obtained in good yield even when large aldehydes are used as the starting material and even when the primary amino groups are macromolecules.

In general, it is essential that the aldehyde, linked to the chelant residue, or to one of its chelates, or salts, by means of an aliphatic chain as described above, is in a molar excess of from 3 to 40 times the number of primary amino groups.

In particular, the procedure according to the present invention includes the reaction of a key intermediate aldehydo derivative, which is a chelant compound of formula (VI)

K—T—CHO  (VI)

where K and T are as described above, or one of its chelates or salts, with a polyamino compound of formula (VII)

L[NH$_2$]m  (VII)

where L and m are as described above, in a reaction medium, under conditions of reductive alkylation, provided (i) the aldehyde of formula (VI) is present in a 3 to 40 fold molar excess with respect to the m primary amino groups; ii) the reaction is carried out in the presence of a reducing agent specific for the imine bond, but not for the aldehyde, the reducing agent being in a 3–60 fold excess with respect to the starting m primary amino groups.

Preferably, the reaction medium is selected from the following: an aqueous buffer, of pH from 5 to 10, a low molecular weight alcohol, an aprotic dipolar solvent, or even a mixture of the two; the temperature of reaction is between −5 and 60° C., for a length of time of between 2 and 170 hours.

A first and particularly preferred realization of the procedure of the present invention envisages:

the use of a metal chelate aldehydo compound of formula (VI), or one of its salts, in a molar excess of about 10–35 fold with respect to the total number of primary amino groups of L;

the reaction medium is an aqueous buffer at a pH of 7–9, or methanol, or a mixture thereof;

the reducing agent is sodium cyanoborohydride;

the temperature ranges between 15–30° C.;

the reaction time is between 10–72 h.

In a second, particularly preferred realization of the procedure of the present invention the reductive alkylation reaction occurs between a chelant aldehydo compound, of formula (VI) and a polyamino compound of formula (VII) as above described, followed by the subsequent formation of the relative metal complex and/or one of its salts.

Key intermediate aldehydes preferred for the preparation of the compounds of the present invention are the compounds of formulae (Ia) and (IIa) below:

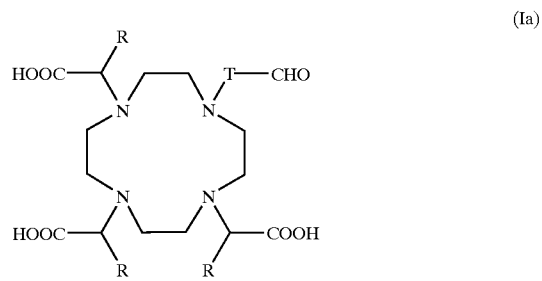

(Ia)

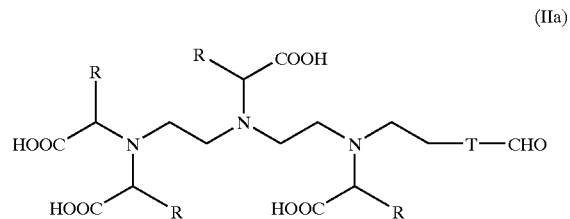

(IIa)

in which T is as above defined and
R is H or CH$_3$ or —CH$_2$—O—Bz or

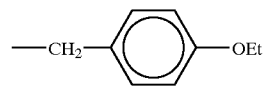

provided that only one of the R substituents is different from H, and compounds (Ia) and (IIa) are either as a chelant or as a complex with a bi- or trivalent metal ion selected from those described previously, or one of their salts.

Particularly preferred key intermediates are the following aldehydes of formula from (IIIa) to (VIa)

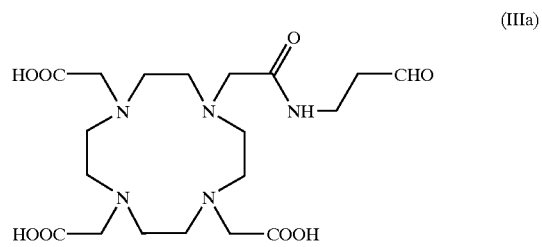

(IIIa)

10-[2-oxo-2-[(3-oxopropyl)amino]ethyl]-1,4,7,10-tetraazacyclododecan-1,4,7-triacetic acid, and its corresponding gadolinium complex of formula (IVa)

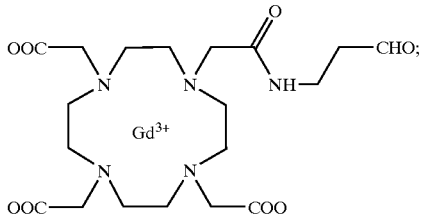

(IVa)

3,6,9,12-tetraaza-11,15-dioxo-3,6,9-tris(carboxymethyl)-pentadecanoic acid of formula (Va), and its relative gadolinium complex of formula (VIa)

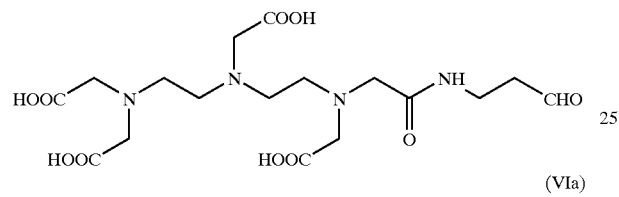

(Va)

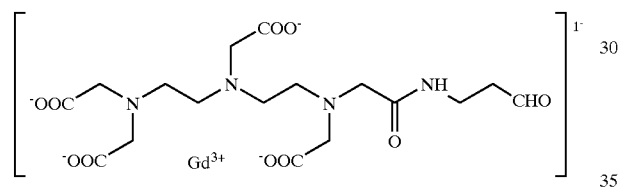

(VIa)

and their salts.

Particularly preferred organic moieties on which to insert the chelants of formula (Ia), (IIa), or their metal complexes, are polyamino derivatives such as diamines and polyamines, diamino acids, polypeptides, polyamino acids, proteins, antibodies, di- and polyamino sugars and linear or branched polymers containing primary amino groups or their derivatives.

Particularly preferred polyamines are for example spermidine, spermine, diethylenetriamine, alkylenediamines, tris-(2-aminoethyl)amine, jeffamine.

Particularly preferred amino acids are lysine and ornithine.

Particularly preferred macromolecules are insulin, chymotrypsinogen A, myoglobin, albumin, cytochrome c, branched and linear polylysine, ramified and linear polyornithine, hormones, growth factors.

Particularly preferred are those products obtained by reaction between the aldeydes compounds of formula (IVa) and (VIa) with the amino derivatives defined previously.

The aldheydes of formula from (Ia) to (VI a) are key intermediate of paramount importance for obtaining the multialkylated compounds of the invention. In particular they made possible the extensive, sometimes exhaustive, dialkylation under strictly controlled and mild reductive conditions, of the desired poliamino derivatives according to the synthetic process of the invention.

The preparation of the preferred key intermediates of the invention is outlined in the following schemes 1 and 2, for the cases in which the R groups are equal to H in the compounds of formula (Ia) and (IIa), while T is as previously defined Scheme 1

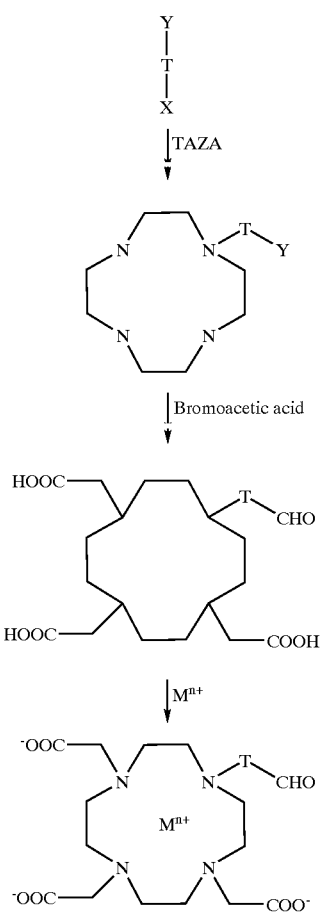

The process illustrated in Scheme 1 can be summarized as follows:

preparation, using known synthetic procedures, of a masked aldehyde building block, corresponding to the formula X—T—Y, where T is as previously defined, X represents a leaving group, preferably selected from the group constituted by halogens, OTs, OMs, Otf, and Y represents an aldehyde protected with a protective group preferably selected from those that are labile at acidic pH, in particular the derivatives of 1,3-dioxolane and 1,3-dioxane;

reaction between TAZA (1,4,7,10-tetraazacyclododecane) and the aldehyde building block prepared above to give a 1:1 alkylation product;

reaction with bromoacetic acid and simultaneous deblocking of the protected aldehyde to give the chelant agents of formula (Ia), in which R=H.

if desired the formation of the desired metal complex and/or of the salts thereof by chelation of the metal ion, preferably carried out by reacting the chelant agents of formula (Ia) with a metal, either in its salt or oxide form, optionally in the presence of a quantity of a base or acid necessary for neutralization to give the relative metal complexes.

Scheme 2

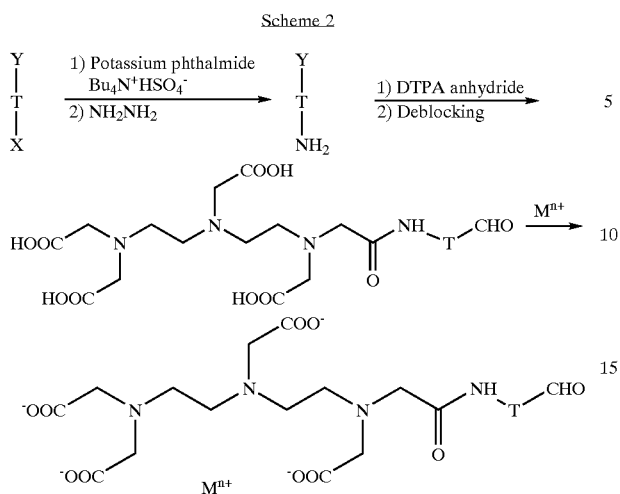

The process illustrated in Scheme 2 can be summarized as follows:

preparation of a masked aldehyde building block, corresponding to the formula X-T-Y, where T is as above defined, X represents a leaving group, preferably selected from the group constituted by halogens, OTs, OMs, Otf, and Y represents an aldehyde protected with a protective group preferably selected from those that are labile at acidic pH, in particular the derivatives of 1,3-dioxolane and 1,3-dioxane;

transformation of X into an amine to give the carbonyl—protected $H_2N$—T—CHO-block;

condensation between a commercially available dianhydride of DTPA (diethylenetriaminepentaacetic acid) with the aldehyde block prepared previously;

deblocking of the protected aldehyde to give the chelant agents of formula (IIa), in which R=H;

optionally forming complexes and their salts as described for Scheme 1.

Unlike the generalized teaching of the state of the art, it has also surprisingly been found not only possible, but indeed highly convenient, to conjugate directly and with high yield the amino or polyamino carriers cited above with metal complexes of the chelants of formula (Ia) and (IIa) rather than with the respective chelants. This is totally unexpected, but particularly advantageous because the products obtained do not require a subsequent complexation step. In this way, an incomplete and/or non-specific incorporation of the metal ions into the complex is avoided. Furthermore, potentially degradable products need not to be subjected to the often very drastic conditions required for complexation, Finally, purification of the final product is much more straightforward.

The reductive alkylation reaction for the preparation of the polychelants/polychelates, objects of the present invention, occurs according to the following conditions:

reaction of a chelant of formula (Ia) or (IIa) or, preferably, of one of their metal complexes, or one of their salts, with the amino carrier of interest in a 3 to 40 fold excess with respect to the total number of primary amino groups "m" of the same, preferably 10–35 fold;

the reaction medium is generally an aqueous buffer such as phosphate, borate, bicarbonate, carbonate, acetate or similar at a pH from 5 to 10; or is constituted by an alcohol of low molecular weight such as, for example, methanol, ethanol, propanols, butanols; or by an aprotic dipolar solvent such as, for example, DMF, DMSO, DMA; a mixture with aqueous buffer solutions such as those mentioned above is also possible and sometimes preferred;

the reaction occurs in the presence of a reducing agent specific for the imine bond, but not for the aldehyde, in a 3–60 fold excess with respect to the amino groups of the starting amino carrier, whereas preferred examples of the reducing agent are sodium cyanoborohydride ($NaCNBH_3$), pyridine borane, trimethylamine borane and analogues; the temperature of the reaction is between −5 and 60° C., but preferably between 15–30° C.; the reaction time varies from 2 to 170 h, but preferably from 10 to 72 h.

Particularly preferred are phosphate and borate buffers at pH values between 7 and 9. Preferred solvents are methanol, DMF and DMSO. The concentration of the amino carrier in the reaction medium is between 0.1 and 40% (w/v). The preferred reducing agent is sodium cyanoborohydride.

Obviously, when the reductive alkylation reaction is carried out starting from the chelant of formula (Ia) or (IIa) with the amino carrier, the subsequent step involves the formation of the relative metal complex, according to known methods and techniques.

A further unexpected advantage of the reductive alkylation of the invention, as opposed to other methods of alkylation, concerns the specificity of the reaction which permits its application to proteins and amino derivatives that contain other reactive groups. The specificity of the reaction has, for example, been confirmed with proteins. In all cases, analysis of the amino acids of the modified proteins, has been shown to be identical to that of the starting protein except for the lysine residue and possibly the amino acid at the amino terminal part of the molecule. The possibility that compounds of formula (Ia) and (IIa) or their metal complexes may react with side chains of other amino acids to give hydrolyzable products, which could escape identification during analysis amino acids, has been excluded.

Indeed, the gadolinium complex of formula (IVa), for example, did not react with a model peptide devoid of free primary amino groups. This experiment was conducted with the luteinizing hormone-releasing hormone, LHRH, a peptide with the amino-terminal group blocked, having the sequence pGlu-His-Trp-Ser-Tyr-Gly-Leu-Arg-Pro-Gly-amide and molecular mass 1182.3. Mass spectrometry has shown that its mass remains unchanged after reaction with the gadolinium complex of formula (IVa) under the conditions adopted for the modification of proteins.

On the contrary, the products that are obtained by reaction of the gadolinium complex of formula (IVa) with the proteins selected for the present invention contain a number of complex residues that is well greater than the number of amino groups theoretically available (□ and ε)

Consequently, a large proportion of the (α and ε)-amino groups have undergone double alkylation and also monoalkylation in a ratio that substantially depends on the reaction conditions adopted (i.e., time, temperature, excess of reagents, etc.).

For example, reaction of the lysine ε-amino groups with gadolinium complex of formula (IVa) gives the modified lysine residues of formula (IX) and (X):

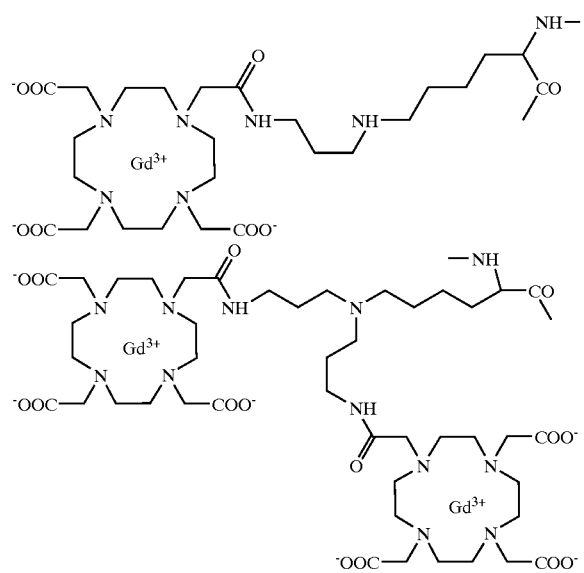

Hydrolysis of such modified residues gives $N^\epsilon$-(3-aminopropyl)lysine and $N^\epsilon,N^\epsilon$-bis(3-aminopropyl)lysine which can be utilized in the characterization of the type of substitution.

As an additional exemplification, Table 1 below illustrates the peculiar advantages of the present invention, in which the products obtained are characterized in terms of the parameter p which is always greater than 1.

Indeed, this value is, for example, equal to 8.1% for the $(DOTA)_{8.79}$cytochrome c product described by Lewis et al. (Bioconj. Chem. 1994, 5, 565–576), assuming complete complexation, while for the derivative of cytochrome c described in Example 11 of the present invention this value is 10.9%. Assuming, for an MRI experiment, the administration of a dose of 100 □mol of Gd/kg, in the case of the product of Lewis et al. a total of 11.4 □mol of product/kg should be administered, while for the product of the present invention only 6.8 □mol/kg (that is, almost half) is required. Actually, the same authors (Lewis et al.) indicate that the efficiency of the chelation with metal ions varies from 84.5 to 97.7% (Bioconj. Chem. 1994,5,565–576, Table 1 pg. 567). Considering that for the product of the present invention this value is 100%, the final benefits are clearly even greater.

The compounds of the present invention have a wide field of application. In particular, the complexes with paramagnetic metals can be used, when suitably formulated, in all diagnostic procedures based on magnetic resonance.

The chelates of the present invention can also be used in. nuclear medicine. In this case, however, the metal ion that is chelated is a radioisotope that emits particles for example $^{51}$Cr, $^{67}$Ga, $^{68}$Ga $^{111}$In, $^{99m}$Tc, $^{140}$La, 175Yb, $^{153}$Sm, $^{166}$Ho $^{90}$Y $^{149}$Pm $^{177}$Lu $^{47}$Sc $^{142}$Pr, $^{159}$Gd or $^{212}$Bi.

The metal complexes of the present invention can also be encapsulated in liposomes, employed as single or multila-

TABLE 1

Comparison of the characteristics of some preferred products of the invention and the state of the art [F = Formula (III)].

| Conjugated product | m | p | n | ρ | Gd (% w/w) | Reference |
|---|---|---|---|---|---|---|
| (Gd-DTPA)n HSA | 60 | 25 | 35 | 1 | 6.5% | Vexler, V. S. et al., Invest. Radiol. 1992, 27, 935–941. |
| (Gd-DTPA)n BSA | 60 | 41 | 19 | 1 | 3.3% | Ogan M. et al., Invest. Radiol. 1987, 22, 665–671 |
| (DOTA)n cytochrome c | 19 | 10.21 | 8.79 | 1 | 8.1% | Lewis, M. R. et al., Bioconj. Chem. 1994, 5,565–576 |
| (Gd-DTPA)nPL | 156 | 116 | 40 | 1 | 15.7% | Berthezene, Y. et al., Invest. Radiol. 1992, 27, 346–351 |
| F3-Lys | 2 | 0 | 3 | 1.5 | 24.3% | The present invention Example 4 |
| F4-Lys | 2 | 0 | 4 | 2 | 24.8% | The present invention Example 5 |
| F5-diethylenetriamine | 2 | 0 | 4 | 2 | 25.4% | The present invention Example 7 |
| Fn-insulin | 3 | 0.1 | 4.6 | 1.59 | 8.5% | The present invention Example 8 |
| Fn-myoglobin | 20 | 0.5 | 27.9 | 1.43 | 13.5% | The present invention Example 9 |
| Fn-chymotrypsinogen A | 15 | 0.2 | 28.2 | 1.91 | 10% | The present invention Example 10 |
| Fn-cytochrome c | 19 | 9 | 14.6 | 1.46 | 10.98 | The present invention Example 11 |

The above table clearly shows that the products obtained according to the teaching of the state of the art are characterized by ρ=1, while those of the present invention have ρ>1 (in some cases up to the maximum value possible, i.e., 2, which means that the complete disubstitution of the primary amino groups of the carrier was obtained). Furthermore the percent content (by weight) of Gd per carrier molecule, is on average much higher for the compounds of the present invention, when the same carriers are compared.

mellar vesicles or used in association with an anionic, hydrophilic and watersoluble "carrier". This "carrier" can be a saccharide, an oligosaccharide, a polysaccharide or a glycosoaminoglycan containing sulphate groups, such as for example heparin sulphate, condroitin sulphate or dermatan sulphate.

Now described are the methods of preparation for compounds illustrative of the present invention.

EXAMPLE 1

Methods

Analytical Methods for the Characterization of the Prepared Compounds

Mass Spectrometric Analysis

The mass value of products of the present invention have been determined using the technique of Electrospray Ionization (ESI-MS), which permits the analysis of metal complexes. The macromolecular-type products were also analyzed using the technique termed Matrix Assisted Laser Desorption Ionization Time Of Flight (MALDI-TOF) with a Lasermat 2000 (Finnigan Mat) instrument and aciano-4-hydroxycinnamic acid (ACH) or sinapinic acid as the matrix.

Elemental Analysis

The percentages of C, H, and N were obtained according to standard methods. The gadolinium content was determined by means of emission spectrometry (ICPES) or x-ray fluorescence (XRF). The samples were completely mineralized in a microwave apparatus prior to the analysis.

Analysis of Amino Acids

In the case of compounds obtained starting from proteins, the protein content was determined by means of quantitative analysis of the amino acids. The analyses were conducted after hydrolysis of the products at 110° C. in 6 N HCl for 20–48 h. The hydrolyzates were analysed on a Carlo Erba 3A-29 analyser, equipped with a ninhydrin post-column detector.

Determination of Free Amino Groups

For the macromolecular type products, the "p" parameter (remaining free amino groups after conjugation) has been determined using an assay based on fluorescamine as described in Stocks S. J., Andrew J. M., Ramey C. W., Brooks D. E., Anal. Biochem., 1986, 154(1), 232–234. The response for the compound under analysis has been compared with that of the corresponding non-modified macromolecule. In the case of compounds obtained starting from proteins, the protein content was determined by quantitative analysis of the amino acids. The concentrations of non-modified proteins were determined on the basis of the absorption coefficient in the case of insulin ($\epsilon 277.5$ nm=0.957 mL·mg$^{-1}$·cm$^{-1}$) and chymotrypsinogen A ($\epsilon 282$ nm=2.03 mL·mg$^{-1}$·cm$^{-1}$), while for myoglobin and cytochrome c the pyridine-hemochromogen method was used (Riggs, A., Methods in Enzymol., 1981, 76, 20–21).

Size Exclusion Chromatography

In the case of compounds obtained starting from proteins, the homogeneity of the product has been verified by size exclusion chromatography. Samples of each compound were injected (25 □L) onto a Superdex 75HR 10/30 column (Pharmacia) equilibrated in 0.2 M NH$_4$HCO$_3$. Chromatography was carried out in a cold room (6–7° C.) at 0.5 mL/min and followed spectrophotometrically at 280 nm.

Relaxivity Measurement

For some Gd-containing products the relaxivity $r_1$ was measured using a Bruker Minispec 120, at 0.5 T and 39° C.

EXAMPLE 2

Gadolinium Complex of 10-[2-Oxo-2-[(3-oxopropyl)amino]etihyl]-1,4,7,10-tetraazacyclododecan-1,4,7-triacetic Acid

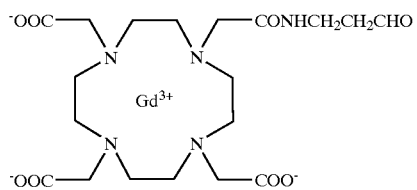

A) 10-[2-oxo-2-[(3-oxopropyl)amino]ethyl]-1,4,7,10-tetraazacyclodode-can-1,4,7-triacetic acid (Compound of formula IIIa)

The product was prepared according to the procedure described in Example 4 of patent application WO 95/32741, page 49.

The $^1$H-NMR, $^{13}$C-NMR, IR and MS spectra are in agreement with the structure indicated.

B) Gadolinium complex of 10-[2-oxo-2-[(3-oxopropyl)amino]ethyl]-1,4,7,10-tetraazacyclododecan-1,4,7-10-tetraazacyclododecan-1,4,7-triacetic acid (Compound of formula IVa)

Gadolinium oxide (1.14 g; 0.00315 mol) is added to a solution of compound A) (2.9 g; 0.0063 mol) in H$_2$O (3000 mL). The reaction mixture is heated to 50° C. for 20 h and the reaction followed by HPLC. The reaction mixture is filtered through a Millipore (0.45 □m) filter. After evaporating to dryness, the desired product is obtained (3.85 g; 0.00627 mol).

Quantitative yield m.p.: >280° C.; Quantification of ethylene glycol (GC): 1.35% (external standard); HPLC titre: 94% (in area %); Titre K.F.: 9.25%; Elemental analysis for C$_{19}$H$_{30}$GdN$_5$O$_8$ 3.18 H$_2$O:

|  | C | H | Gd | N |
| --- | --- | --- | --- | --- |
| calculated | 33.74 | 5.51 | 23.25 | 10.36 |
| Found | 33.36 | 5.67 | 23.30 | 10.16 |

EXAMPLE 3
Gadolinium Complex of N$^\alpha$-Carbobenzyloxy-N$^\epsilon$,N$^\epsilon$-bis-[4-aza-5-oxo-6-(1,4,7,10-tetraazacsclododecyl-4,7,10-triacetate)hexyl]-L-lysine

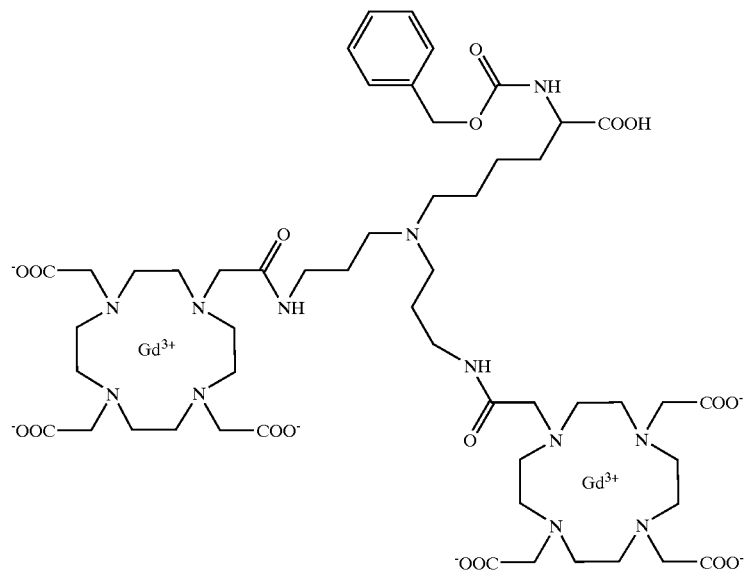

This example shows that even in conditions of high steric hindrance, in this case due to the presence of a carbobenzyloxy group on the α amino of L-lysine, the dialkylation of the ε amino group is very easily obtained.

4 g of compound (IVa) obtained as described in Example 2B (6.5 mmol) are dissolved in 10 mL of methanol and cooled to −5° C., in a nitrogen atmosphere. Separately, a solution of 0.45 g of Nα-carbobenzyloxy-L-lysine (Z-lysine, 1.6 mmol) and 0.1 g KOH is prepared in 4 mL of MeOH. This is added to the solution of compound (IVa) obtained as described in Example 2B in the flask. Finally, 0.6 g of NaCNBH$_3$ (9.5 mmol) are added. The mixture is then stirred constantly at −5° C. for 18 h. The solvent is then evaporated and the residue taken up with 10 mL of a mixture of CH$_3$CN/H$_2$O trifluoroacetic acid (TFA) 10:90:0.1. This is then filtered to eliminate the insoluble residue and purified on a LiChrosorb RP-18 25×250 mm column (E. Merck). The pure compound is eluted isocratically with the same CH$_3$CN/H$_2$O/TFA mixture. The homogeneous fractions are combined on the basis of an analysis carried out under the same conditions on the analytical column and then evaporated to dryness. The residue is washed with ether and driedunder vacuum. Approximately 1.9 g of the desired product is obtained containing traces of TFA.

K.F. titre: 3.43% (w/w); HPLC titre: 98% (in area %); Column: E. Merck LiChrospher 100 RP-18 (5mm); 250×4 mm; Eluent A: 5 mM phosphate pH 3; Eluent B: CH$_3$CN; 10 min 10%B; gradient from 10 to 30% B in 10 min. Flow rate: 1 mL/min; Elemental analysis:

|  | C | H | N | Gd |
|---|---|---|---|---|
| % calculated: | 33.03 | 3.97 | 6.80 | 12.72 |
| % found: | 33.22 | 3.88 | 7.28 | 12.15 |

ESI-MS spectrum: 1476 (MH+).

To demonstrate the structure of the product, it is hydrolysed in 6 N HCl for 20 h at 110° C.

The hydrolysis product is N$^\epsilon$,N$^\epsilon$-bis(3-aminopropyl)-lysine as confirmed by mass spectrometry (MH+: 261) and NMR spectrometry. During chromatography on the LiChrosorb RP-18 (25×250 mm) column, fractions containing the monoalkylation product are also collected.

Yield: 14% (200 mg); ESI-MS spectrum: 879 (MH+).

EXAMPLE 4

Gadolinium Complex of $N^{\square},N^{\epsilon},N^{\epsilon(a)}$-Tris-[4-aza-5-oxo-6-(1,4,7,10-tetraazacyclododecol-4,7,10-triacetate)hexyl]-L-lysine

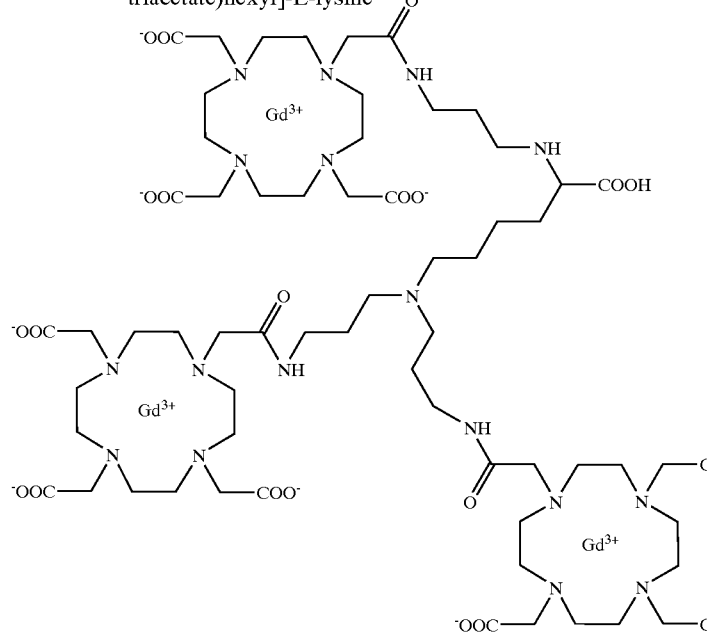

2 g of compound (IVa) obtained as described in Example 2B (3.25 mmol) are dissolved in 10 mL methanol and cooled to −5° C. A solution of 100 mg lysine-HCl (0.55 mmol) and 26 mg LiOH (1.1 mmol) in 4 mL methanol and, finally, 310 mg of NaCNBH$_3$ (4.93 mmol) are then added to this. The reaction mixture is stirred at −5° C. for 60 h, at which point the solvent is evaporated, and the residue taken up in 5 mL H$_2$O. This is filtered and purified on an ion exchange resin (AG-50W-X4, Bio-Rad) equilibrated in 0.1 M pyridine/acetic acid pH 5.6. After removing excess product (IVa) and by-products of the reaction from the column, the product of interest is eluted with 1 M pyridine/acetic acid pH 5.6. The fractions containing product (TLC: Silica 60-F254, Eluent: ethanol/25% ammonia 1:1; Rf=0.36) are combined, dried, taken up in water and lyophilised extensively. 425 mg of product are obtained (40% of the lysine). MALDI-TOF MS: 1943 (MH+ calculated 1940).

Relaxivity $r_1$=5.25 s$^{-1}$ mM$^{-1}$ on a per gadolinium basis.
The ρ ratio for the product described in this example is 1.5.

EXAMPLE 5

Gadolinium Complex of $N^{\square},N^{\square},N^{\epsilon},N^{\epsilon}$-Tetrakis-[4-aza-5-oxo-6-(1,4,7,10-tetraazacyclododecyl-4,7,10-triacetate)hexyl]-L-lysine

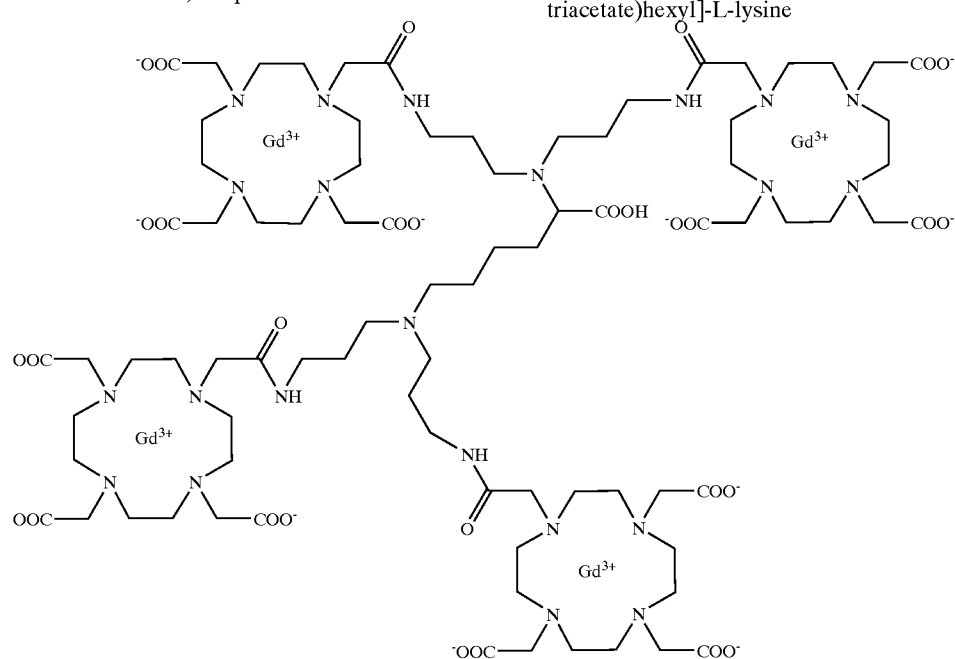

2 g of compound (IVa) obtained as described in Example 2B (3.25 mmol) are dissolved in 10 mL methanol and cooled to −5° C. in a flask equipped with a reflux condenser. A solution of 75 mg lysine HCl (0.41 mmol) and 20 mg LiOH (0.82 mmol) in 3 mL methanol and then 310 mg of NaCNBH$_3$ (4.93 mmol) are added. After stirring at −5° C. for 4 h, the mixture is left under constant stirring at ambient temperature (21° C.) for a further 40 h. A further 0.5 g of compound (IVa) (0.82 mmol) dissolved in 2 mL methanol and 77 mg of NaCNBH$_3$ (1.23 mmol) are then added. This is then heated for 2 h at 50° C. and then left at ambient temperature for 17 h. Three mL of H$_2$O are added to dissolve the residue formed and this is again heated to 50° C. for 3 h, before being left for 18 h at ambient temperature. The solvent is evaporated and the residue taken up in 5 mL H$_2$0, filtered and purified on an ion exchange resin (AG-50W-X4, Bio-Rad) equilibrated in 0.1 M NH$_4$HCO$_3$. After removing excess product (IVa) and by-products of the reaction from the column, the product of interest is eluted with a 0.1–2 M gradient of NH$_4$HCO$_3$.

The fractions containing the tri- and tetraalkylation products (TLC: Silica 60-F254, Eluent: ethanol/25% ammonia 1:1; Rf=0.36) are combined, dried and taken up in 3 mL water. This is then purified by preparative HPLC on a LiChrosorb RP-18 (250×25 mm) column, eluting the product with a 5 to 20% gradient of acetonitrile containing 0.1% TFA. After a few fractions containing the trisubstituted product, the fractions containing the desired product are collected. These are dried, taken up in water and lyophilised extensively.

Yield: 90 mg. MALDI-TOF MS: 2543 (MH+calculated 2538).

Relaxivity r$_1$=8.35 5−1 mM$^{-1}$ on a per gadolinium basis.

The ρ ratio for the product described in this example is 2.

EXAMPLE 6

N$^\alpha$-Carbobenzyloxy-N$^\epsilon$,N$^\epsilon$-bis-[4-aza-5-oxo-6-(1,4,7,10-tetraazacyclododecyl-4,7,10-triacetate)hexyl]-L-lysine Three g of compound (IIIa) obtained as described in Example 2A (6.5 mmol) and 2 g triethylamine are dissolved in 10 mL of methanol and then cooled to −5° C., in an atmosphere of nitrogen. Separately, a solution of 0.45 g of N-carbobenzyloxy-L-lysine (Z-lysine, 1.6 mmol) and 0.1 g KOH are prepared in 4 mL of MeOH. This is then added to the flask. Finally 0.6 g of NaCNBH$_3$ (9.5 mmol) are added and the mixture maintained under constant stirring at −5° C. for 18 h. The solvent is evaporated and the residue taken up with 10 mL of a mixture of CH$_3$CNIH$_2$O/trifluoroacetic acid (TFA) 10:90:0,1. This is filtered to remove the insoluble residue and purified on a LiChrosorb RP-18 25×250 mm column (E. Merck) eluting the product isocratically with the same CH$_3$CN/H$_2$O/TFA mixture. The homogenous fractions are combined on the basis of an analysis carried out under the same conditions on the analytical column and then evaporated to dryness. The residue is washed with ether and dried under vacuum. 1.3 g of the desired product is obtained containing traces of TFA.

K.F. titre: 4.85% (w/w); HPLC titre: 96% (in area %) (method as in Example 3); ESI-MS spectrum: 1168 (MH+);

The following derivatives have been obtained in an analogous way:

N$^\alpha$N$^\epsilon$,N$^{\epsilon(\alpha)}$-tris-[4-aza-5-oxo-6-(1,4,7,10-tetraazacyclododecyl-4,7,10-triacetate)hexyl]-L-lysine N$^\alpha$,N$^\alpha$,N$^\epsilon$,N$^\epsilon$-tetrakis-[4-aza-5-oxo-6-(1,4,7,10-tetraazacyclododecyl-4,7,10-triacetate)hexyl]-L-lysine Subjecting the product described in the present example to hydrogenation gives the following derivative: N$^\epsilon$,N$^\epsilon$-bis-[4-aza-5-oxo-6-(1,4,7,10-tetraazacyclododecyl4,7,10-triacetate)hexyl]-L-lysine.

EXAMPLE 7

Gadolinium Complex of 1,1,4,7,7-Pentakis-[4-aza-5-oxo-6-(1,4,7,10-tetraazacvclododecyl-4,7,10-triacetate)hexyl]-1,4,7-triazaheptane 1.5 g of compound (IVa) obtained as described in Example 2B (2.44 mmol) are dissolved in 10 mL of 0.1 M boric acid and then 11 □L of diethylenetriamine (0.1 mmol) are added; the final pH of this solution is 8.5 and does not further adjustment. Sodium cyanoborohydride (300 mg, 4.8 mmol) is then added and the reaction mixture is stirred under nitrogen for 6 h at room temperature and for 60 h at 37° C. At this point the turbid reaction mixture is transferred into a dialysis membrane (Cellusep H1, nominal cut-off 1000 obtained from Membrane Filtration Products, Inc.) and extensively dialysed against water. Mass spectrometry analysis showed the presence of two main peaks at about 2500 and 3100, corresponding respectively to diethylenetriamine-(compound IV)$_4$ and diethylenetriamine-(compound IV)$_5$. The dialysed reaction mixture was lyophilized, dissolved in 1 mL of 50 mM phosphate buffer pH 5.5, 0.1 M Na$_2$SO$_4$ and loaded on a 2.2×120 cm column of Sephadex G-25, equilibrated in the same buffer. The first peak was collected, concentrated by lyophilization, dialysed against water and finally lyophilized, yielding 90 mg of the fully alkylated derivative (MH+ found -and calculated= 3092).

EXAMPLE 8

Procedure for the Conjugation of Compound (IVa) with Insulin 95 mg of compound (IVa) obtained as described in Example 2B and 15 mg of NaCNBH$_3$ are added to a solution of 20 mg of porcine insulin, sodium salt (Calbiochem n. 407696, Mr 5778; 10 μmol amino groups) in 13 TnL of borate buffer 0.1 M, pH 8. After 4 h of reaction at 20° C. a further 95 mg of compound (IVa) and 15 mg of NaCNBH$_3$ are added.

The conjugation reaction takes place at a total molar ratio of 30:1 of compound (IVa) with respect to the amino groups present and at 1.5:1 between the NaCNBH$_3$ and compound (IVa). After a further 16 h at ambient temperature, the conjugate is separated from the excess of reagent and from the by-products of reaction by size exclusion chromatography on a Sephacryl S-100HR column (Pharmacia). The column (45×8.9 cm) is eluted with 0.15 M NH$_4$HCO$_3$ at 20 mL/min. The final product is concentrated and desalted by ultrafiltration/diafiltration on an Amicon YM-3 membrane.

The product is homogenous as assessed by size exclusion chromatography (t$_R$=24.99 min). Treatment with fluorescamine has revealed the presence of only 0.1 mol NH$_2$ groups/mol protein. The Gd content is 4.6 mol/mol protein. Mass spectrometry revealed signals corresponding to the mass of insulin plus, respectively, 2, 3, 4 and 5 residues of compound (IVa). Amino acid analysis (see following Table 2) reveals excellent agreement with the composition of non-modified insulin, with the exception of the amino acids lysine, glycine and phenylalanine which are reduced by one unit. Since the latter two amino acids are the amino terminals of the two chains of insulin, this confirms that both the α- and ε-amino groups take part in the reaction. The low quantity of cysteine found is due to the typical instability of this amino acid under hydrolytic conditions and has not been considered.

TABLE 2

Analysis of the amino acids of the insulin compound (IVa) conjugate

|     | Theoretical | Found | D (Found Theoretical) |
| --- | --- | --- | --- |
| Asx | 3 | 3.04 | 0.04 |
| Thr | 2 | 1.94 | −0.06 |
| Ser | 3 | 2.70 | −0.30 |
| Pro | 1 | 1.27 | 0.27 |
| Glx | 7 | 7.29 | 0.29 |
| Gly | 4 | 3.09 | −0.91 |
| Ala | 2 | 1.99 | −0.01 |
| Cys | 6 | 4.53 | −1.47 |
| Val | 4 | 4.30 | 0.30 |
| Met | — | — | |
| Ile | 2 | 1.87 | −0.13 |
| Leu | 6 | 5.97 | −0.03 |
| Tyr | 4 | 3.92 | −0.08 |
| Phe | 3 | 2.09 | −0.91 |
| His | 2 | 1.99 | −0.01 |
| Lys | 1 | 0.17 | −0.83 |
| Arg | 1 | 0.99 | −0.01 |

The ρ ratio for the product described in this example is 1.59.

EXAMPLE 9

Procedure for the Conjugation of Compound (IVa) with myoglobin

The procedure is the same of Example 8, using horse heart myoglobin (commercially available from Sigma, n. M-1882, Mr 17567) and borate buffer pH 8.5. The quantities used are:

0.5 g myoglobin (0.56 mmol $NH_2$) in 100 mL buffer 10.37 g compound(IVa) obtained as described in Example 2B added in two lots (16.9 mmol) 1.6 g $NaCNSH_3$ added in two lots (25.4 mmol).

The product has been shown to be homogenous upon analysis by size exclusion chromatography ($t_R$=19.58 min). Treatment with fluorescamine has revealed the presence of only 0.5 mol NH2 groups/mol protein. The Gd content is 27.9 mol/mol protein. Mass spectrometry has revealed signals corresponding to the mass of myoglobin plus, respectively, from 29 to 33 residues of compound (IVa).

Amino acid analysis, used to determine the protein content of the prepared compound, has shown that the composition of the treated myoglobin is in excellent agreement with the composition of non-modified myoglobin, with the exception of lysine, which, instead of there being 19 residues, was shown to be next to zero.

Relaxivity $r_1$=19 $s^{-1}$ $mM^{-1}$ on a per gadolinium basis.

The ρ ratio for the product described in this example is 1.43.

EXAMPLE 10

Procedure for the Conjugation of Compound (IVa) with Chymotrypsinogen A

The procedure is the same as Example 8, using bovine pancreas chymotrypsinogen A (commercially available from E. Merck, n. 2306, Mr 25656) and borate buffer pH 9. The quantities used are:

0.5 g chymotrypsinogen A (0.29 mmol NH2) in 100 mL buffer 5.38 g compound (IVa) obtained as described in Example 2B added in two lots (8.77 mmol)

0.82 g $NaCNBH_3$ added in two lots (13.2 mmol).

The product has been shown to be homogenous upon analysis by size exclusion chromatography ($t_R$=19.55 min). Treatment with fluorescamine has revealed the presence of only 0.2 mol NH2 groups/mol protein. The Gd content is 28.2 mol/mol protein. Mass spectrometry has revealed a widened signal whose centre corresponds to the mass of chymotrypsinogen A plus 26.6 residues of compound (IVa).

Amino acid analysis, used to determine the protein content of the prepared compound, has shown that the composition of the treated chymotrypsinogen A is in excellent agreement with the composition of non-modified chymotrypsinogen A, with the exception of lysine, which, instead of there being 14 residues, was shown to be next to zero.

The ρ ratio for the product described in this example is 1.91.

EXAMPLE 11

Procedure for the Conjugation of Compound (IVa) with Cxochrome c

The procedure is the same of Example 8, using horse heart cytochrome c (commercially available from Sigma, n. C-7752, Mr 12360). The quantities used are:

20 mg cytochrome c (32 μmol $NH_2$) in 10 mL buffer 0.55 g compound (IVa) obtained as described in Example 2B added in two lots (0.9 mmol)

100 mg $NaCNBH_3$ added in two lots (1.6 mmol).

Prior to purification by column, the reaction mixture is first dialysed against borate buffer to remove unreacted $NaCNBH_3$ and then treated with potassium ferricyanide (final concentration 5 mM) to reoxidise the ferroion of the same group.

The product has been shown to be homogenous upon analysis by steric exclusion chromatography. As it was not possible to treat the product with fluorescamine because of interference on the part of the heme group, the free amino groups were determined with TNBS (Habeeb A. F. S. A. Anal. Biochem., 1966, 14, 328–336) which gave a value of 9 mol NH2 groups/mol protein. The Gd content was 14.6 mol/mol protein. Mass spectrometry revealed a widened signal in which 3 peaks were visible corresponding to the mass of cytochrome c plus 15, 16 and 17 residues of compound (IVa).

The ρ ratio for the product described in this example is 1.46.

EXAMPLE 12

Procedure for the Conjugation of Compound (IIIa) with Insulin

Compound (IIIa) of Example 2(A), 70 mg, (0.155 mmol) is added to a solution of 10 mg of porcine insulin, sodium salt (Calbiochem n. 407696, Mr 5778; 5.2 μmol amino groups) in 7 mL of borate buffer 0.1 M pH 8, with the pH maintained at 8 with 1 N NaOH. 15 mg of $NaCNBH_3$ are then added and the mixture left under constant stirring at ambient temperature for 20 h.

The reaction mixture is concentrated by ultrafiltration (Amicon YM-3 membrane) and then loaded on a Sephacryl S-100HR column (Pharmacia). The column (2.2×100 cm) is eluted with 0.15 M $NH_4HCO_3$ at 1 mL/min. The final product is concentrated and desalted by ultrafiltration/ diafiltration on an Amicon YM-3 membrane.

The product has been shown to be homogenous upon analysis by steric exclusion chromatography.

Treatment with fluorescomine has revealed the presence of only 0.3 mol $NH_2$ groups/mol protein.

Mass spectrometry has revealed signals corresponding to the mass of insulin plus, respectively, 2, 3, and 4 residues of compound (IIIa).

By integration of the signals the mean number of substituents is calculated to be 3.4. The p ratio for the product described in this example is 1.26.

The following derivatives were obtained using the same procedure:

[Formula III]myoglobin

[Formula III]cytochrome c

[Formula III]chymotrypsinogen A

EXAMPLE 13

Procedure for the Conjugation of Compound (IIIa) with Polylysine 1 g of compound (IIIa) of example 2A) (1.6 mmol) is added to a solution of 10 mg of polylysine bromohydrate (Sigma n. P0879, Mr 1000–4000; 52 μmol amino groups, assuming a mean of 10 Lys residues and $M_r$ 2108, based on MALDI-TOF MS analysis) in 7 mL of borate buffer, 0.1 M pH 8, with the pH maintained at 8 with 1 N NaOH. 150 mg of $NaCNBH_3$ are then added and the mixture left under constant stirring for 72 h at ambient temperature.

The reaction mixture is then loaded on a Sephacryl S-1OOHR column (Pharmacia). The column (8.9×45 cm) is then eluted with 0.15 M $NH_4HC0_3$ at 20 mL/min. The first peak is concentrated by evaporation and then lyophilized (52 mg).

Mass spectrometry (MALDI-TOF) has revealed a wide distribution of signals in the region between 7000 and 13000, centered around 9600 which corresponds to the mean mass of polylysine plus 14 units of compound (IIIa).

Treatment with fluorescamine has revealed the presence of only 1.2 mol NH2 groups/mol protein, assuming Mr=9600.

What is claimed is:

1. A compound of formula (I):

$$L[NH_2]_p[NHF]_z[N[F]_2]_x \quad (I),$$

in which

L is a polyaminic organic moiety;

F is a —$CH_2$—T—K group, representing a chelant/ chelate residue, where

T is a $C_{2–C5}$ aliphatic chain, interrupted or not by one or more heteroatoms selected from O, N, S or by functional groups selected from carbonyl, thiocarbonyl, amide, ester, thiourea, thioamide groups, said chain being linked covalently to an atom of a residue K, K is a tetraazacyclododecyl containing group, or one of its metal chelates, or one of its salts and where the total number of the F groups is 3 to 2 m;

| | |
|---|---|
| p | is a number from 0 to m − 2, |
| z | is a number from 0 to m− 1, and |
| x | is a number from 1 to m, | where m is a number from 2 to 1000, m being the total number of the primary amino groups originally present on L and where p+x+z=m, with the proviso that, when x=1, then z≠0, and in which the chelated metal ions are bi- or trivalent paramagnetic ions or radioisotopes.

2. A compound of formula (I):

$$L[NH_2]_p[NHF]_z[N[F]_2]_x \quad (I),$$

in which:

L is selected from a group consisting of spermidine, norspermidine, spermine, 4,9-dioxadodecandiamine, 3,6-dioxaoctandiamine, an alkylenediamine, diethylenetriamine, triethylenetetramine, tris-(2-aminoethyl)amine, jeffamine, N-glucosamine, lysine and its derivatives, ornithine and diamino sugars;

F is a —$CH_2$—T—K group, representing a chelant residue, where

T is a $C_2$–$C_5$ aliphatic chain, containing an amido or carbonylamino group, said chain being linked covalently to a nitrogen atom of a K residue, K is a tetraazacyclododecyl containing group a tetraazacyclododecyl containing group, its derivatives, metal chelates or salts, in which the metal ion chelates are selected from the bi- or trivalent ions of elements having atomic numbers between 20 and 31, or 39, 42, 43, 44, 49, or between 57 and 83 or the ions of the following radioisotopes $^{51}Cr$, $^{67}Ga$, $^{68}Ga$, $^{111}In$, $^{99m}Tc$ $^{40}La$, $^{175}Yb$, $^{153}Sm$, $^{166}Ho$, $^{90}Y$, $^{149}Pm$ $^{177}Lu$ $^{47}Sc$ $^{142}Pr$, $^{159}Gd$ and $^{212}Bi$ and where the total number of the F groups is 3 to 2 m;

| | |
|---|---|
| p | is a number from 0 to m − 2, |
| z | is a number from 0 to m − 1, and |
| x | is a number from 1 to m, | where m is a number from 2 to 1000, m being the total number of the primary amino groups originally present on L and where p+x+z=m, with the proviso that, when x=1, then z≠0, and in which the chelated metal ions are bi- or trivalent paramagnetic ions or radioisotopes.

3. A compound according to claim 2, in which the metal ions are selected from $Mn^{(2+)}$, $Fe^{(3+)}$, $Gd^{(3+)}$, $Eu^{(3+)}$, $Dy^{(3+)}$, $In^{(3+)}$ and $^{99m}Tc^{(3+)}$.

4. A compound according to claim 2, in which F is a chelant residue of formula:

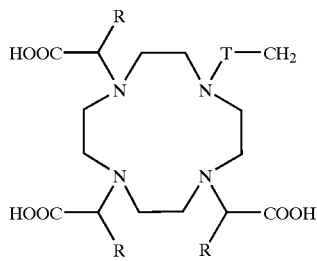

in which T is as defined and
R is H or CH$_3$ or CH$_2$—O—Bz or

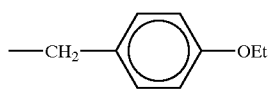

provided that only one of the R substituents is different from H, as well as their metal chelates, or their salts.

5. A compound according to claim 4, in which F is a residue of formula (II) or (III)

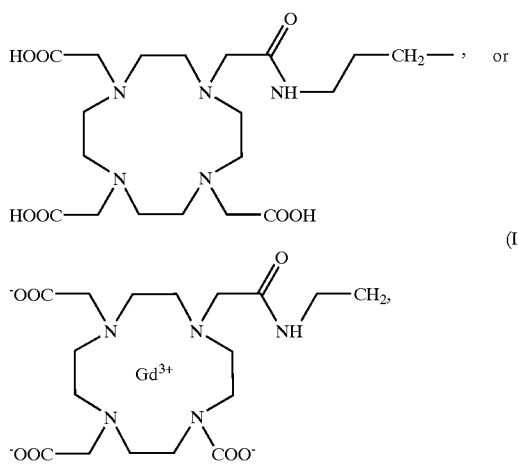

or one of its salts.

6. A compound according to claim 5, selected from the group consisting of:

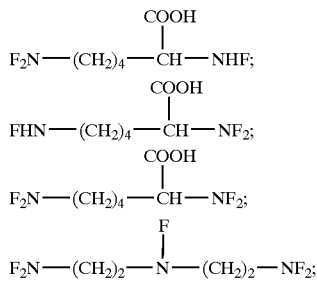

where F is a chelant residue of formula (II)

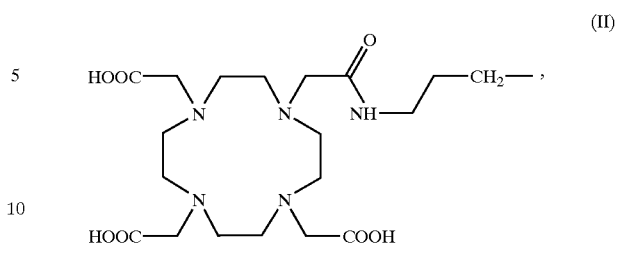

or a chelate of formula (III)

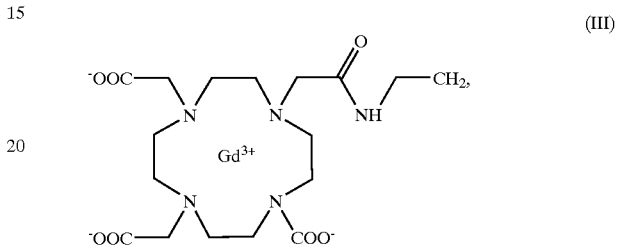

or a salt thereof.

7. A process for preparing a compound of claim 1 comprising reacting a chelant compound of formula (VI)

where K, T are as described above, or a chelate, or a salt thereof, with a polyamino compound of formula (VII)

where L and m are as described above, in a reaction medium, under conditions of reductive alkylation, provided that the aldehyde of formula (VI) is present in a 3 to 40 fold molar excess over the number m of primary amino groups, and the reaction is conducted in the presence of a reducing agent specific for the imine bond, but not for the aldehyde, said reducing agent being present in a 3–60 fold excess with respect to the total number of primary amino groups.

8. The process according to claim 7, in which said reaction medium is selected from an aqueous buffer, at a pH from 5 to 10, a low molecular weight alcohol, an aprotic dipolar solvent, or mixtures thereof.

9. The process according to claim 8, in which the reaction temperature is between –5 and 60° C. for a length of time of between 2 and 170 h.

10. A process according to claim 7, in which:
a chelate of formula (VI), or one of its salts, is employed in a molar excess of about 10–35 fold with respect to the total number of amino groups;
the reaction medium is an aqueous buffer at a pH of 7–9, or methanol, or a mixture of the two;
the reducing agent is sodium cyanoborohydride;
the temperature is variable between 15–30° C.; and
the reaction time is between 10–72 h.

11. A process according to claim 7, in which the reductive alkylation reaction occurs between a chelant of formula (VI) and the polyamino residue of formula (VII), followed by the subsequent formation of the corresponding metal complex and/or one of its salts.

12. A pharmaceutical and/or diagnostic composition comprising as active ingredient at least one of the compound of claim 1, or one of its physiologically compatible salts, together with pharmaceutically acceptable carrier or diluent or excipient.

13. A pharmaceutical composition for radiotherapy, comprising a compound of claim 1 together with pharmaceutically acceptable carrier, diluent and/or excipient.

14. A contrastographic diagnostic composition for magnetic resonance imaging, comprising a compound of claim 1 together with pharmaceutically acceptable carriers diluent and/or excipient.

15. A contrastographic diagnostic composition for scintigraphy, comprising a compound of claim 1 together with pharmaceutically acceptable carrier diluent and/or excipient.

16. A method of radio therapy, NMR imaging or scintigraphy, comprising administering to a subject to be treated or imaged an effective amount of a compound of claim 1.

* * * * *